United States Patent

Ratner et al.

[11] Patent Number: 6,143,027
[45] Date of Patent: Nov. 7, 2000

[54] POLYMERIC INTRAOCULAR LENS MATERIAL HAVING IMPROVED SURFACE PROPERTIES AND INTRAOCULAR LENS CONSTRUCTION

[75] Inventors: Buddy D. Ratner; Nancy B. Mateo, both of Seattle, Wash.

[73] Assignee: Washington Research Foundation, Seattle, Wash.

[21] Appl. No.: 07/041,796

[22] Filed: Apr. 23, 1987

Related U.S. Application Data

[63] Continuation-in-part of application No. 06/768,895, Aug. 23, 1985, abandoned.

[51] Int. Cl.[7] ............................................. A61F 1/16
[52] U.S. Cl. ................................................ 623/6
[58] Field of Search ........................... 623/5, 6, 66

[56] References Cited

U.S. PATENT DOCUMENTS

| | | |
|---|---|---|
| 4,170,043 | 10/1979 | Knight et al. . |
| 4,188,426 | 2/1980 | Aurbach ................................. 427/40 |
| 4,373,218 | 2/1983 | Schachar . |
| 4,655,770 | 4/1987 | Gupta et al. ............................ 623/6 |
| 4,656,083 | 4/1987 | Hoffman et al. . |
| 4,666,445 | 5/1987 | Tillay ........................................ 623/6 |
| 4,681,585 | 7/1987 | Sayano et al. .......................... 623/6 |

FOREIGN PATENT DOCUMENTS

| | | |
|---|---|---|
| 0172618A3 | of 0000 | European Pat. Off. . |
| WO8701040 | of 0000 | European Pat. Off. . |
| WO 7900326 | 6/1979 | WIPO . |

OTHER PUBLICATIONS

Millard "Plasma Synthesis of Fluor. Films" J. of Appl. Polym. Science, vol. 17, pp. 2501–2507 (1973).

Millard, Windle and Pavlath, "Plasma Synthesis of Fluorocarbon Films," Jnl. Applied Polymer Science, vol. 17, pp. 2501–2507 (1973).

*Primary Examiner*—David Isabella
*Attorney, Agent, or Firm*—Lowe, Price, LeBlanc & Becker

[57] ABSTRACT

An intraocular lens is described that includes an optic portion formed of an optically suitable polymer or glass material that has been coated by a fluorocarbon polymer. A haptic portion of the IOL is attached to the optic. The resulting low-energy IOL surface induces significantly reduced cell damage when contacted with corneal endothelial tissues. The fluorocarbon polymer coating is preferably applied by exposing IOL surfaces to a plasma formed from a gaseous fluorocarbon monomer. The resulting IOL causes substantially less damage to corneal endothelial cells during implantation.

27 Claims, 2 Drawing Sheets

POLYMERIC INTRAOCULAR LENS MATERIAL HAVING IMPROVED SURFACE PROPERTIES AND INTRAOCULAR LENS CONSTRUCTION

This application is a continuation-in-part of Ser. No. 768,895 filed Aug. 23, 1985, now abandoned and assigned to Washington Research Foundation of Seattle, Wash., the contents of which are hereby incorporated by reference in their entirety.

TECHNICAL FIELD

The field of the invention is intraocular lenses and their construction. More particularly, the invention is directed to lenses that have modified surface properties that substantially improve their suitability as intraocular implants.

BACKGROUND OF THE INVENTION

Treatment for cataracts and other diseases of the eye often requires removal of the natural lens form the eye. An artificial intraocular lens, in many cases, is surgically implanted to perform the visual focusing function of the removed defective natural lens. The intraocular lens (IOL) is composed of the optical lens body and a haptic device or element for positioning and securing the optical lens body in proper position within the eye. The lens body portion of IOLS in recent years has been formed of glass or polymeric materials that possess the appropriate optical qualities and that remain chemically and mechanically stable after implantation over a long period of time. The exact design of the haptic device depends upon the location within the eye at which the optic lens is to be placed. Three general designs are posterior chamber lenses, anterior chamber lenses, and iris plane lenses. The wide variety of IOL haptic element designs is shown in the literature, examples of which are Hoffer U.S. Pat. No. 4,244,060; Sheets U.S. Pat. No. 4,328,595; Feaster U.S. Pat. No. 4,418,431; Bayers U.S. Pat. No. 4,316,293; and Kelman U.S. Pat. No. 4,174,543 and U.S. Pat. No. 41,340,979.

A major difficulty with IOLs has been that the implantation process can cause serious injury to the corneal endothelium, which may result in corneal edema. Adhesive contact between the most commonly used intraocular lens body optical material, poly(methyl methacrylate) (PMMA), and the corneal endothelium during surgical implantation results in losses of endothelial cells that do not regenerate. Cell loss has been directly related to the number of times the intraocular lens contacts the endothelium during surgery, with approximately 20% loss resulting from each contact.

The relationships between cell adhesion and surface properties of the optic lens body such as surface energy, surface chemistry and surface rigidity have been studied by many investigators. Surface modification of the PMMA surface substrate has been shown to alter lens adhesiveness to cells. For example, Knight et al. in U.S. Pat. No. 4,170,043 describes reduced corneal endothelium damage for lenses coated with a water soluble film, such as polyvinyl alcohol, that is self-sacrificing in protecting the endothelium during implantation but dissolves away within 24 hours.

The literature discussing suitable IOL optic materials and implantation techniques reports that hydrophilic surfaces result in less cell adhesion damage during implantation than hydrophobic surfaces. Thus, much work is reported in which optic material surfaces are altered to achieve a more hydrophilic character than PMMA.

Investigators have used gamma radiation grafting to polymerize hydroxyethyl methacrylate (HEMA) and vinyl pyrolidone (VP) onto a PMMA substrate. Using a laboratory "touch test" between the modified lens material and rabbit corneas, it was discovered that PMMA alone induces 10–30% damage, a PMMA/HEMA graft about 10% damage and a PMMA/VP graft less than 10% cell damage. However, these "touch tests" are relatively arbitrary and nonreproducible.

Another investigator studied silicone coated lenses, using as a test an 18-gram weight to press a sample intraocular lens and rabbit cornea together for 10 seconds to produce a consistent force on the endothelium. It was reported that PMMA caused "considerable damage", silicone resin lenses induced "less damage" than PMMA, and silicone elastomer created "far less damage". No quantitative comparisons of cell damage between the samples were possible.

In yet another study, the investigator constructed and employed an instrument directly measuring the force of adhesion between rabbit corneal endothelium and intraocular material samples. The average stress calculated for PMMA was 0.66 g/cm$^2$ which was shown to be the highest of all materials studied. A plasma-deposited VP coating on PMMA and a conventional coating of Healon™ (manufactured by Pharmacia Inc.) on PMMA each lowered the stress to 0.19 g/cm$^2$. Two hydrogels poly (HEMA) and Duragel™ (Soflex), exhibited the lowest stresses, 0.09 and 0.14 g/cm$^2$, respectively, of the materials tested.

Thus, the best state-of-the-art coatings discovered prior to the present invention appear to result from surfaces that are soft, hydrophilic hydrogels. However, hydrogel surfaces, such as HEMA and VP, while demonstrating lower cell damage relative to the PMMA substrate and other coatings tried, exhibit a number of disadvantages. For example, the coatings are soft and easily damaged. Also, they are difficult to package and difficult to hydrate properly at surgery. Further, hydrogels are prone to calcification and bacterial contamination. Thus, the IOL constructions known prior to the present invention may still cause significant damage during implantation or may be otherwise unsuitable for general use.

DISCLOSURE OF THE INVENTION

It is an object of the invention to provide an improved intraocular lens construction that remedies the major disadvantage of the conventional intraocular lens, e.g. adhesion damage to corneal endothelium cells during surgical implantation.

The improved intraocular lens of the invention includes an optical lens body formed from a material having suitable optical qualities and coated with a fluorocarbon polymer coating that is bound covalently to lens body surfaces. The intraocular lens also includes a haptic element portion that secures the lens body in position in the eye.

The fluorinated coating on the lens body is a dense, impermeable, cross-linked film that reduces the degree of endothelial cell adhesion damage during the implantation procedure. It may also protect the lens body from degradation caused by environmental conditions. In addition, the fluorinated film may prevent leaching of defusible components from the lens material into the eye. The fluorinated coating can be deposited on the haptic element as well as the lens body. Because any area of the IOL might contact corneal endothelial cells as the IOL is implanted, coating all exposed surfaces is advantageous to cell damage reduction. Reduced iris abrasion may also result.

A preferred intraocular lens body is a poly(methyl methacrylate) material shaped to perform the IOL optical functions. The fluorocarbon polymer surface coating is preferably deposited onto the lens body by exposing it to a gaseous fluorocarbon monomer and an electrical field. The field ionizes the monomer gas, creating a fluorocarbon plasma. The plasma reacts with the optic material, resulting in the simultaneous polymerization of the fluorocarbon groups and their attachment onto the lens body surfaces.

A preferred process for making the lens body includes selecting an optically suitable material such as poly(methyl methacrylate) and shaping it to perform its optical task. The shaped optic is placed in a chamber containing a gaseous fluorocarbon monomer, such as perfluoropropane. A radio-frequency generator induces an oscillating electric field within the chamber, polymerizing the monomer and attaching the polymer film to the surface of the substrate.

PREFERRED EMBODIMENTS

Figure 1:
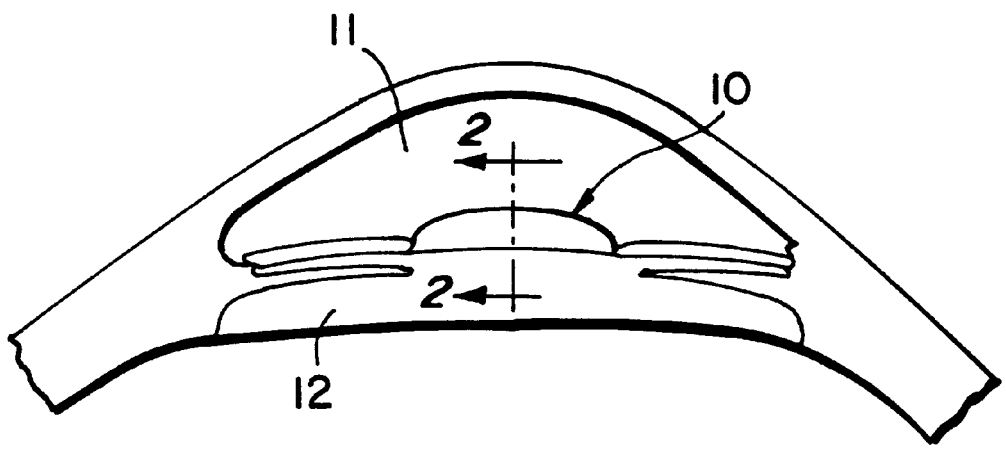
FIG. 1 is a schematic view of an intraocular lens that is coated according to the invention and positioned within the anterior chamber of the human eye.
Figure 2:
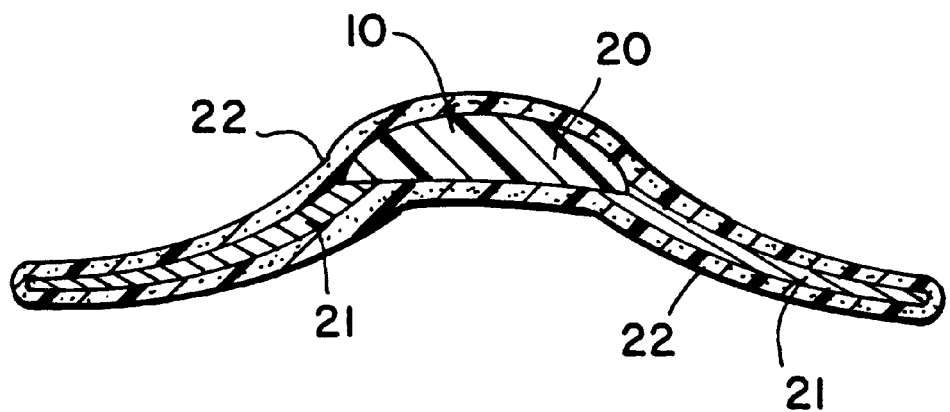
FIG. 2 is a sectional view of the intraocular lens of FIG. 1 in which all IOL surfaces, including the haptic element, are coated.

An intraocular lens (IOL) 10 of the invention is shown in FIG. 1 positioned in the anterior chamber 11 of the human eye after surgical implantation to replace the natural lens that had been removed from the posterior chamber 12. The lens 10 is shown in cross-sectional view in FIG. 2. The IOL includes a lens body 20 that substantially performs the visual focusing functions of a removed natural lens.

The lens body 20 may be any material that is optically satisfactory and remains chemically and mechanically stable indefinitely. A preferred conventional lens material, as noted above, is poly(methyl methacrylate) (PMMA). This material transmits more than 90% of incident light and is easily machined, molded and polished to the appropriate optical shape. The material is also nontoxic, strong, lightweight, chemically inert and optically stable.

The IOL of the invention also includes a haptic element or device 21 that functions to secure the optic lens body in proper position within the eye. The exact design of the haptic 21 depends upon where within the eye the the lens is to be located. In addition to the anterior position shown in FIG. 1, an IOL may be positioned in the posterior chamber. Alternatively, the IOL may include a clip-like haptic device that positions the IOL adjacent to the iris. The haptic device may be bonded or otherwise fastened to the optic. Alternatively, the haptic device may be formed as an extension of the lens itself.

The IOL of the invention includes a fluorocarbon polymer coating 22 that covers all surfaces of the optic portion of the IOL that might contact the corneal endothelium during surgical implantation. A lens having the fluorocarbon polymer coating of the invention causes substantially less damage to corneal endothelial cells which it may contact during implantation than a conventional lens. Thus, fluoropolymer coated lenses represent a substantial advantage over uncoated IOLs or those coated with materials other than a fluorocarbon polymer. The fluorinated plasma coating can be deposited on all optic and haptic surfaces or only on specific areas, such as optic only, depending on the design of the holder which secures the IOL in the reach on chamber.

The preferred fluorocarbon polymer coating is a thin film covalently bonded to the lens surfaces. The film is highly cross-linked and substantially impermeable but does not adversely affect the optical qualities of the optic portion of the IOL. However, the film is of a thickness that presents a uniform and distinct modification of surface properties of the optic material. The film is not so thick a layer that internal stresses can destroy the coating. For example, in coating a series PMMA lenses in a perfluoropropane plasma, film thicknesses on the order of 200–500 Angstroms were found to be satisfactory.

The fluorinated coating is preferably applied by exposing the IOL to a gas plasma formed from a fluorocarbon monomer. For example, a conventional PMMA IOL may be coated by exposing it to a gas plasma of perfluoropropane. Any flurocarbon or fluorinated hydrocarbon monomer that forms a polymer film of similar composition is suitable. Gaseous fluorocarbon monomers and mixtures thereof are preferred.

The plasma reactor may be of conventional design. A reactor may include a glass chamber for holding the IOLs to be treated. The chamber is surrounded by capacitance plates or rings coupled to a radio-frequency generator which establishes an oscillating electric field within the chamber. The IOL surfaces to be coated are first etched by exposure to an argon plasma, then the IOLs are exposed to a plasma containing the monomer to be polymerized and deposited on the IOL surfaces. System parameters of RF power, gas mixture, chamber pressure and reaction time may be varied to control the rate of the reaction and depth of deposition. The parameters selected depend on the character of the monomers employed.

The following examples further describe the fluorocarbon polymer surface coatings of the IOL optic that result in reduced corneal endothelial cell damage during implantation, the plasma gas deposition process for forming such coatings and a comparison of the IOL surface of the invention with surfaces previously known in the art.

Example 1 PMMA lens material, PERSPEX disks fabricated by CooperVision of Seattle, Wash., were selected to represent the optic portion of an IOL. These disks were exposed to a range of gaseous monomers, including perfluoropropane, an embodiment of the fluorocarbon polymers suitable for producing the coating on the IOLs of the invention. In addition to the perfluoropropane monomer of the invention, tests were run using ethylene oxide (EO), N-vinyl-2-pyrrolidone (NVP) and hydroxyethyl methacrylate (HEMA), as representative of prior art IOLs.

The resulting products were characterized in terms of surface chemistry and surface energy. Cell damage resulting from contact of the lens coated optical material of the invention with corneal tissue was measured and compared with the untreated PMMA lens material substrate and the other treated surfaces. The measured surface characteristics of the material of the invention as a function of cell damage were compared with measurements of the same properties for the other surfaces.

Electron Spectroscopy for Chemical Analysis (ESCA) was used to determine elemental composition and bonding states of the outermost 100 Angstroms of the polymer surface. A survey scan at 1–1000 eV was taken to determine the various elements present. Then, scans in specified eV ranges were made to obtain the spectra of the elements C, O, F and N.

As a means of characterizing the surface energy of the material of the invention and comparable materials, the "critical surface energy" was determined using the method of Zisman, as described in "Relation of the Equilibrium Contact Angle to Liquid and Solid Constitution", *Advances in Chemistry Series No. 43*, Fowkes, Editor, American Chemical Society, Washington, D.C. pp. 1–51 (1964). The analysis required measuring contact angles of various purified liquids on each type of surface at atmospheric conditions. Cosines of the measured angles were then plotted as a function of the surface tensions of the test liquids, resulting in a Zisman plot from which the critical surface energy was calculated.

Actual interaction of the modified surface of the invention with corneal endothelium was determined by employing an apparatus which produced consistent and quanitatively comparable results between samples.

Figure 3:
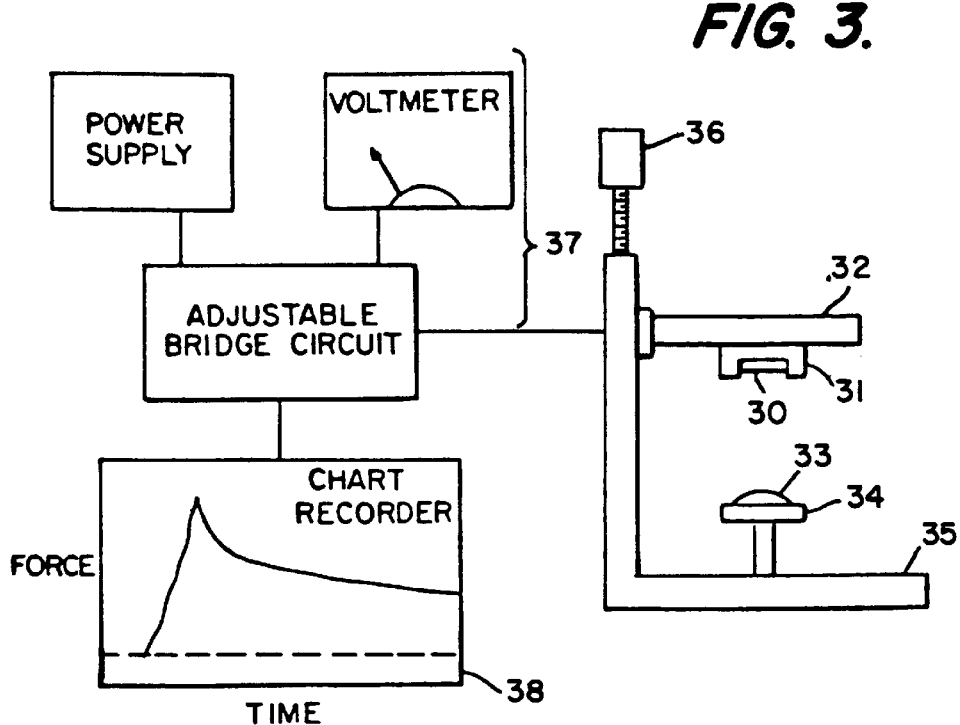
FIG. 3 is a schematic diagram of an instrument for contacting an intraocular lens body with corneal tissue to determine potential corneal endothelium damage.

Referring to FIG. 3, the device used in this test is shown schematically. A disk 30 of the material to be tested is secured in a holder 31 mounted on the lever arm 32 of a microforce detector 37. A freshly excised rabbit cornea 33 is mounted in a holder 34 on a base 35 opposed to the disk 30 to be tested. A micrometer 36 is provided to advance the lever arm 32 and the disk sample 30 into contact with the corneal button 33 at a measurable force. An electronic circuit of the microforce detector 37 measures the contact force, reporting the measurement on a chart recorder 38.

In operation the test disk 30 was brought into contact with the corneal tissue by means of the micrometer 36 for a period of 40–60 seconds. The initial maximum force under which contact was made was recorded. The corneal buttons were then removed, stained and examined under a low power microscope. The percent damaged cells were counted and recorded.

Example 2 PMMA lens material, PERSPEX™ disks fabricated by CooperVision of Seattle, Wash., in the form of 10 mm diameter disks was selected. Monomers of perfluoropropane and ethylene oxide both manufactured by Matheson Chemical Company of Newark, Calif., N-vinyl-2-pyrrolidone manufactured by Alfa Products of Danvers, Mass. and hydroxyethyl methacrylate manufactured by Hydron Industries were prepared.

Sample disks were placed approximately 6 cm downstream of the capacitance plates and the continuous system was evacuated to 0.035 Torr. Argon was introduced at 0.25 Torr. RF generator power at 50 watts was continued for five minutes to allow etching of the PMMA substrate. After evacuating the reactor, the fluorocarbon monomer gas was introduced at the desired pressure. For perfluoropropane monomer, the pressure was 0.25 Torr and the generator power was maintained at 30 watts for 10 minutes. Afterwards, the chamber was evacuated to 0.035 Torr and then gradually brought up to atmospheric pressure by introduction of argon and air.

Two ESCA spectrometers, a Hewlett Packard Model 5950-B at University of Utah and a Surface Science Model SSX-100 at University of Washington, were used to determine the chemical nature of the surfaces of the intraocular lens material samples. Spectra from the HP-5950-B were resolved using a DuPont 310 curve resolver, while spectra from the SSX-100 were resolved with a peak-fitting routine on an HP-9836-C computer. The C(ls) hydrocarbon peak was assigned to 285 eV and used as a reference peak to correct for any energy shifts. The ESCA results of the samples measured appear in section 2 of the following table.

TABLE 1

Elemental and Bonding Ratios

| Compound | C/O | C/N | C/F | CH | C—O | C=O | C—O | C—N | C—N |
|---|---|---|---|---|---|---|---|---|---|
| 1. Stoichiometry based on monomer structure | | | | | | | | | |
| PMMA | 2.5 | — | — | 60 | 20 | — | 20 | — | — |
| HEMA | 2.0 | — | — | 50 | 33.3 | — | 16.7 | — | — |
| NVP | 6.0 | 6.0 | — | 50 | — | — | — | 33.3 | 16.7 |
| Ethylene Oxide | 2.0 | — | — | — | 100 | | | | |
| | | | | | $CF_3$ | $CF_2$ | $CFCF_n$ | CF | C—$CF_n$ |
| Perfluoropropane | — | — | 0.375 | | 33.3 | 33.3 | — | 33.3 | — |
| 2. ESCA Results | | | | | | | | | |
| PMMA | 3.0 | — | — | 58 | 23 | — | 19 | — | — |
| pHEMA (a) | 2.4 | — | — | 46 | 38 | — | 16 | — | — |
| HEMA (b) | 2.2 | — | — | 46.5 | 31 | — | 23.5 | — | — |
| pNVP (c) | 8.0 | 8.0 | — | 43.2 | — | — | — | 29.7 | 27.1 |
| NVP (b) | 5.7 | 3.1 | — | 53 | — | — | — | 34 | 13 |
| Ethylene Oxide (b) | 4.8 | — | — | 61 | 21 | 9 | 9 | — | — |
| | | | | | $CF_3$ | $CF_2$ | $CFCF_n$ | CF | C—$CF_n$ |
| Perfluoropropane (b) | — | — | 0.52 | 4.0 | 28.0 | 27.6 | 15.6 | 13.3 | 11.5 |

Notes
(a) Poly(HEMA) spun on glass coverslips (2% in DMF).
(b) Plasma-deposited film on PMMA disk.
(c) Poly(NVP) spun on glass coverslip (2% in methanol).

The contact angles of various purified liquids on each type of surface were measured under atmospheric conditions using a Rame-Hart goniometer, Model 110-00-00NRL Experimentally determined values of the critical surface energy, c, for the several surfaces tested are presented in Table II. Teflon™ and Mylar™ were examined as reference surfaces.

TABLE II

Critical Surface Tensions ($_c$) of Soild Surfaces

| Surface | $_c$ (ergs cm$^{-2}$) |
|---|---|
| Teflon ™ (TFE) | 20.0 ± 1.3 |
| Mylar ™ | 46.7 ± 0.3 |
| PMMA | 37.8 ± 3.2 |
| Perfluoropropane film | 8.1 ± 3.1 |
| Ethylene Oxide film | 45.4 ± 2.7 |
| HEMA film | 49.4 ± 4.1 |
| NVP film | 48.0 ± 4.3 |

Example 3

The samples produced and characterized in Example 2 were contacted with corneal tissue by means of the apparatus of FIG. 3.

Each cornea, rimmed by 2–3 mm of sclera, was excised from a 2–3 kg New Zealand white rabbit and immediately placed in RPMI 1640 media with HEPES buffer, L-Clutamine, and penicillin-streptomycin (Grand island Biological). The cornea in solution was placed in a Forma Scientific Hydrojac $CO_2$ incubator for at least 30 minutes. In preparation for a test, the cornea was removed from this solution, rinsed in a 0.9% NaCl solution, placed on a concave Teflon™ block, and trephined to form a 9-mm-diameter button. The cornea was then placed endothelial side up, in a convex stainless steel holder of the apparatus of FIG. 3. A circle of endothelium 7 mm in diameter was exposed with the center projected 2 mm above the level of the holder edge. A 0.9% NaCl solution was dropped intermittently onto the cornea to keep the cells continuously moist.

A 10-mm-diameter sample disk was mounted in the stainless steel holder of the apparatus which clamped the edges, leaving a 9-mm-diameter exposed planar surface. This holder was then attached to the micro-force detector 32, Deflection Sensor Cartridge, Model DSC3, manufactured by Imperial Controls. The system was calibrated using 1–20 gram weights, depending on the force anticipated for each test. The test range was 4000–20,000 dynes.

The corneal holder was placed directly beneath the lens sample, and the two surfaces were brought into contact with the micrometer attachment. After 40–60 seconds, the cornea and the sample were separated. The cornea was immediately placed in a 0.9% NaCl solution. The initial and maximum force with which contact was made was recorded. Controls for the test were corneal buttons which remained in the holder for 20 minutes and were kept moist with 0.9% NaCl solution. These corneas were subjected to all handling except for actual contact with a sample disk.

To inspect the endothelium, the staining method of Spence and Peyman, described in "A New Technique for the Vital Staining of The Corneal Endothelium," *Invest. Ophtalmol,* 15, No.12 (1000) 1976, involving a combination of Trypan Blue and Alizarin Red S stains provided by Sigma Chemical of St. Louis, Mo., was used. The cornea was then examined under a low power X100 microscope. A central 9 cm$^2$ area, divided into 900 grids, was observed consistently for each cornea. The undamaged and damaged cells were counted.

The PMMA substrate and the treated disks were measured for cell damage over a range of contact forces. The results were then plotted showing cell damage as a function of contact force. Table III reports the best fit curves for the data for each sample. The data are also plotted in FIG. 4.

TABLE III

Best Fits for Cell Damage Data

| Surface | Slope | Intercept | Average |
|---|---|---|---|
| PMMA | 0.00190 ± 0.000494 | −1.65 ± 5.4 | — |
| HEMA | 0.000498 ± 0.000190 | 1.99 ± 2.2 | — |
| NVP | 0.000646 ± 0.000239 | 1.27 ± 2.7 | — |
| Ethylene Oxide | 0.001240 ± 0.000565 | 17.44 ± 6.1 | — |
| Perfluoropropane | — | — | 6.96 ± 3.83 |

As shown in Table I of Example 1, the ESCA results of both conventional and plasma-deposited polymers are compared with stoichiometry of the monomers. The untreated PMMA disk exhibits C/O ratios close to the expected ratio from stoichiometry. The types of bonding present in the sample also compare closely. Each of the HEMA and NVP plasma-deposited coatings shows a close resemblance in composition and bonding to the stoichiometry and to the model poly(HEMA) and poly(NVP) conventional films spun on glass. The peaks comprising the ESCA spectra of the conventional HEMA and NVP polymer surfaces are more distinct than those in the spectral envelopes of the plasma-deposited films. The more ill-defined spectra of the plasma-deposited films reflect the wider distribution of structures, the increased number of chemical species, and the increased cross-linking, all of which are characteristic of plasma depositions. However, the similarity of these plasma deposits to the conventional polymers may indicate a higher level of molecular polymerization (i.e. free radical polymerization through the double bond) than atomic polymerization. This similarity also suggests a comparable regularity of structure which is important to the hydrogel character of conventional poly(HEMA) and poly(NVP). Hence, the coatings deposited by the HEMA and NVP plasmas exhibit hydrogel behavior.

Coatings deposited by ethylene oxide and perfluoropropane plasmas are vastly altered from the monomer structures. These plasmas undergo complex reactions involving "atomic polymerization", a type of deposition in which the molecular structure of the monomer is not retained in the polymer. As a result, a regularity in the structure of the ethylene oxide plasma coating is not likely to occur because the bonding environments noted by ESCA are so dissimilar to those in conventional poly(ethylene oxide).

Referring to Table II of Example 2, the plasma-altered surfaces exhibit definite changes in wettability compared to the PMMA substrate. The fluorinated plasma rendered the disk nonwettable. The other three plasma-deposited surfaces show an increase in wettability as the critical surface tension increases. These results are consistent with the trends reported in the literature, to the effect that wettability decreases with an increase in fluorination and increases with an increase in nitrogen or oxygen bonded to carbon.

Figure 4:
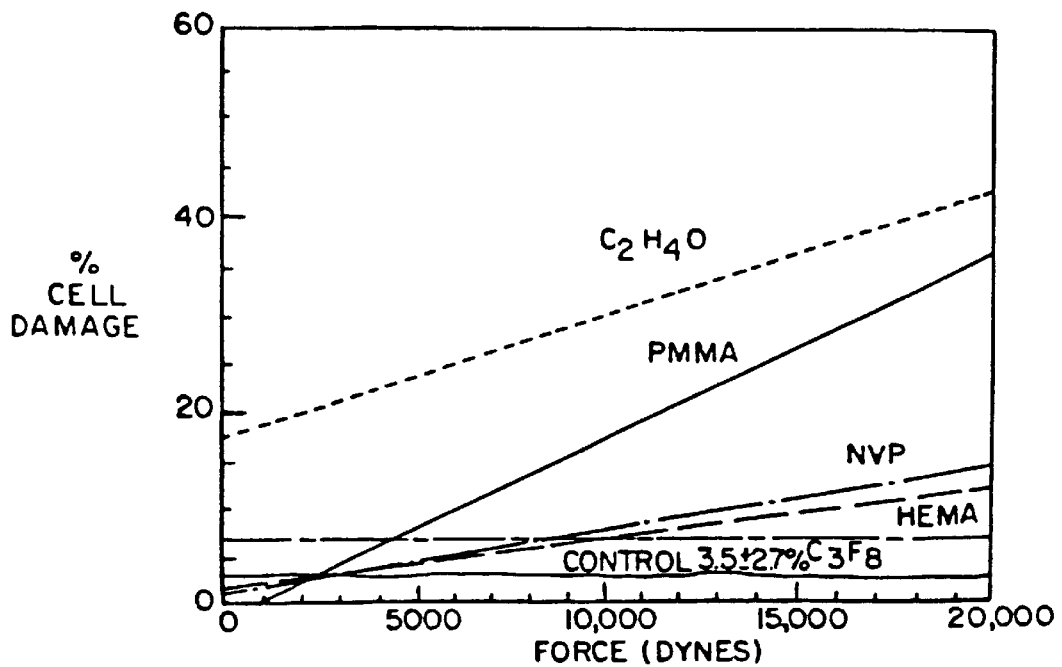
FIG. 4 presents percent corneal cell damage as a function of initial force of contact with tested intraocular lens bodies.

In FIG. 4, percent cell damage is plotted as a function of initial force for each type of surface contacted with corneal tissue by means of the apparatus shown in FIG. 3 and described in Example 3. The solid horizontal line at 3.5±2.7% represents the average damage associated with the control corneas. The lines shown for the other samples are the best curves for the force-damage data, representing either a least squares fit or an average of cell damage where damage appears independent of force. Table III reports the parameters and errors of the fits of these data.

The choice of fit was based on results from the "f test for chi-square" which determines whether adding a term dependent on force (least squares line) is an improvement from the average damage line. PMMA, ethylene oxide, NVP and HEMA surfaces displayed a trend of increasing damage with increasing force, and the least squares fits were plotted. Since the slope of the perfluoropropane force-damage curve was not significantly different from zero, the average cell damage value was plotted.

The parameter values shown in Table III were used to calculate the significance of the differences in the cell adhesion associated with the five surfaces. Relative to PMMA, each of the four data sets was found to have greater than 97% probability that the difference between the fit for PMMA and for an altered surface fit is significant.

The fluorinated surface of the invention induced the lowest endothelial damage over the entire force range investigated. Damage appears to be independent of force.

The HEMA and NVP surfaces were also associated with decreased cell damage, compared to the unmodified PMMA. However, both HEMA and NVP surfaces induced increasing cell damage with increasing force. The ethylene oxide coating caused significantly greater adhesion damage to the cornea than PMMA.

As shown, the degree of cell adhesion damage is significantly changed by modifying the PMMA surface. Changes in the surface chemistry and surface energy have been documented by the ESCA and contact angle studies reported in Example 2.

In summary, the data demonstrate a change in surface properties of poly(methyl methacrylate) material modified by RF plasma deposition. The degree of endothelial cell adhesion to the surface is considerably altered. The percent cell damage as a function of the initial force of contact for each modified surface was significantly different than that induced by PMMA. The results suggest that a rigid, low-energy fluorinated surface is desirable for reduced cell adhesion.

Any glass or polymeric substrate for which low cell adhesion properties are desired and upon which a fluorocarbon monomer may be plasma deposited can be improved by modifying its surfaces according to this invention. Such substrates include glass, polypropylene, poly(methyl methacrylate) and silicone polymers, for example. Fluorocarbon monomers or mixtures thereof which can be deposited on a substrate using the gas plasma technique are within the scope of the invention. Preferred monomers include perfluoropropane, perfluoropropene, hexafluoroethane, and tetrafluoroethylene.

In addition to surface modifications of IOLs by fluoropolymer RF plasma environments, the present invention includes other treatments that might superficially create a surface similar to the one heretofore and in the parent U.S. application. These include:

1. Ion Beam Sputtering of Surfaces: See D. W. Dwight and S. R. F. McCartney, American Chemical Society Materials Science and Engineering Preprints, 50 459–461, 1984, the contents of which are hereby incorporated by reference. A Teflon surface is eroded (sputtered) with an accelerated ion beam. The material sputtered off this Teflon, if allowed to condense on another surface, will resemble the coating prepared by RF-plasma deposition.

2. Fluorocarbon Films by Ultraviolet Surface Photopolymerization. See M. M. Millard, J. Appl. Polym. Sci., 18 3219–3225, 1974, the contents of which are hereby incorporated by reference. Transparent low energy fluoropolymer films are formed on glass slides upon exposure to the vapors from various fluorinated organics in the presence of UV radiation. The surface spectrum obtained using the ESCA technique on these films is significantly different from that of the previously-described plasma method. Still, the technology produces a fluorine-rich overlayer.

3. Transparent Fluorocarbon-Based Semi-II IPN Elastomers by High Energy Radiation Methods. See J. D. Lipko, H. F. George, D. A. Thomas, S. C. Hargest and L. H. Sperling, Journal of Applied Polymer Science, 23, 2739–2755, 1979, the contents of which are hereby incorporated by reference. Interpenetrating polymer networks (IPN's) are formed by exposing a substrate elastomeric polymer to fluorine-containing organic monomers in the presence of gamma or beta radiation. A fluorine-rich surface layer might be produced, and, the quality of the film could be significantly different from that of the plasma method.

4. Method for Producing Fluorocarbon finished on Fibrous Structures, see M. S. Toy, R. S. Stringham, L. C. Fogg, U.S. Pat. No. 4,278,703, Jul. 14, 1981, contents of which are incorporated by reference. Textiles are contacted with a gaseous mixture of fluoroolefins in an inert diluent gas in the presence of UV light. A fluorine-rich surface film will be formed that will more closely resemble that produced in reference 2. above, than to what the RF-plasma method synthesizes.

In fact it is within the scope of the present invention to use any known technology for fluorinating surfaces.

What is claimed is:

1. An intraocular lens comprising a lens formed from polymethyl methacrylate and having an outer surface layer defined by a relatively inert fluorocarbon chemically bonded with respect to the lens.

2. An intraocular lens comprising a lens body formed from a polymeric material, said lens body including a substantially uninterrupted outer surface layer defined by a relatively inert fluorocarbon.

3. A method of producing an intraocular lens comprising the steps of:

forming a transparent lens body from a polymeric material selected to have a predetermined set of optical properties; and forming an outer surface layer substantially completely covering the lens body, the outer surface layer including a relatively inert fluorocarbon to substantially reduce the toxicity of the lens when implanted into the eye.

4. An intraocular lens, comprising:

(a) a lens body of an optically transparent, biocompatible material;

(b) haptic means connected to the lens body for engaging interior eye surfaces for holding the lens in place in the eye; and (c) a hydrophobic coating over said lens body for reducing corneal endothelial cell damage during implantation.

5. The intraocular lens of claim 4, wherein the lens body is formed of a material selected from the group consisting of glasses and polymeric materials.

6. The intraocular lens of claim 4, wherein the hydrophobic coating is a fluorocarbon polymer coating bound covalently to all surfaces to the lens body.

7. The intraocular lens of claim 6, further comprising:
said fluorocarbon polymer covalently bound to and covering said haptic means.

8. The intraocular lens of claim 5 wherein said polymeric material forming the lens body is poly(methyl methacrylate).

9. The intraocular lens of claim 5 wherein said fluorocarbon polymer coating is a fluorinated hydrocarbon.

10. The intraocular lens of claim 5 wherein said fluorocarbon polymer coating is produced from a perfluoropropane monomer.

11. The intraocular lens of claim 5 wherein said fluorocarbon polymer is produced from a perfluoropropene monomer.

12. An improved intraocular lens (IOL) that causes low corneal endothelial cell damage during implantation, comprising:
a lens body, optically shaped for visual focusing with the eye, formed of a material selected from the group consisting of glasses and polymeric materials;
a fluorocarbon polymer coating bound covalently to all surfaces of said lens body; and
a haptic element attached to said lens body, said haptic element engaging interior eye surfaces such that said lens body is fixed in position for visual focusing.

13. An improved intraocular lens that causes low corneal endothelial cell damage during implantation, comprising:
a lens body of poly(methyl methacrylate) optically shaped for visual focusing within the eye;
an impermeable surface coating covalently bound to surfaces of said lens body by exposing said lens body to a monomer of perfluoropropane and an electric field which ionizes and causes plasma polymerization of said monomer and attachment to said lens body surfaces; and
a haptic element attached to said lens, said device engaging interior surfaces of said eye such that said intraocular lens is fixed in position within the eye for visual focusing.

14. An improved intraocular lens that causes low corneal endothelial cell damage during implantation, comprising:
a lens body of an optical material shaped for visual focusing within the eye;
a coating of a fluorocarbon polymer covalently bound to surfaces of said lens body; and
a haptic element attached to said lens body, said element engaging interior surfaces of said eye such that said intraocular lens is fixed in position within the eye for visual focusing.

15. An intraocular lens comprising:
an optical lens body;
a fluorocarbon coating on said lens body; and
a haptic means attached to said lens body for remedially positioning said lens body in the eye.

16. The lens of claim 15 wherein said lens body is formed of a material selected from the group consisting of glasses and polymeric materials.

17. The lens of claim 16 wherein said polymeric material is poly(methyl methacrylate).

18. The lens of claim 15 wherein said fluorocarbon coating is covalently bound to the surface of said lens body.

19. The lens of claim 15 wherein said fluorocarbon coating covers at least a portion of the surface of said haptic means.

20. The lens of claim 15 wherein said fluorocarbon coating forms an impermeable coating on all exposed surfaces of said lens body.

21. The lens of claim 15 wherein said haptic means comprises a plurality of haptic loops attached to said lens body and extending out therefrom.

22. The lens of claim 15 wherein said lens body is formed from a material selected from the group consisting of glass, poly(methyl methacrylate), polypropylene, and silicone polymers.

23. The lens of claim 15 wherein said coating has a thickness of 200–500 Angstroms.

24. An intraocular lens comprising:
an optical lens body;
a haptic element attached to said lens body for remedially positioning said lens body in the eye;
said lens body and said haptic element forming an intraocular lens assembly; and
a fluorocarbon coating on at least a portion of said intraocular lens assembly.

25. The lens of claim 24 wherein said fluorocarbon coating covers the exterior surfaces of said haptic element.

26. The lens of claim 24 wherein said fluorocarbon coating covers the exterior surfaces of said lens body.

27. An intraocular lens comprising:
an optical lens body;
a haptic element attached to said lens body for remedially positioning said lens body in the eye;
said lens body and said haptic element forming an intraocular lens assembly; and
a rigid, hydrophobic coating on at least a portion of the surfaces of said intraocular lens assembly which reduces cell damage when contacted with corneal endothelial tissue.

* * * * *